(12) United States Patent
Boue et al.

(10) Patent No.: US 9,227,898 B2
(45) Date of Patent: Jan. 5, 2016

(54) POSTHARVEST PRODUCTION AND ENHANCEMENT OF RESVERATROL AND PICEATANNOL IN SUGARCANE

(71) Applicants: Stephen M. Boue, New Orleans, LA (US); Matthew E. Burow, New Orleans, LA (US); Deepak Bhatnagar, New Orleans, LA (US)

(72) Inventors: Stephen M. Boue, New Orleans, LA (US); Matthew E. Burow, New Orleans, LA (US); Deepak Bhatnagar, New Orleans, LA (US)

(73) Assignee: The Administrators of the Tulane Edcational Fund, New Orleans, LA (US)

( * ) Notice: Subject to any disclaimer, the term of this patent is extended or adjusted under 35 U.S.C. 154(b) by 0 days.

(21) Appl. No.: 14/375,132

(22) PCT Filed: Jan. 28, 2013

(86) PCT No.: PCT/US2013/023510
§ 371 (c)(1),
(2) Date: Jul. 28, 2014

(87) PCT Pub. No.: WO2013/113033
PCT Pub. Date: Aug. 1, 2013

(65) Prior Publication Data
US 2015/0005533 A1 Jan. 1, 2015

Related U.S. Application Data

(60) Provisional application No. 61/591,724, filed on Jan. 27, 2012.

(51) Int. Cl.
| | |
|---|---|
| *C07C 37/68* | (2006.01) |
| *C10L 1/02* | (2006.01) |
| *C10L 5/44* | (2006.01) |
| *A01H 5/04* | (2006.01) |
| *G21K 5/00* | (2006.01) |

(52) U.S. Cl.
CPC *C07C 37/68* (2013.01); *A01H 5/04* (2013.01); *C10L 1/02* (2013.01); *C10L 5/445* (2013.01); *G21K 5/00* (2013.01)

(58) Field of Classification Search
None
See application file for complete search history.

(56) References Cited

U.S. PATENT DOCUMENTS

| | | | |
|---|---|---|---|
| 2004/0111760 | A1 | 6/2004 | Chia |
| 2008/0268097 | A1 | 10/2008 | Hurst |
| 2009/0208544 | A1 | 8/2009 | Ennamany et al. |
| 2010/0297718 | A1 | 11/2010 | Deinhammer et al. |

OTHER PUBLICATIONS

M. Adrian et al., "Stilbene Content of Mature Vitis Vinifera Berries in Response to UV-C Elicitation", "Journal of Agricultural and Food Chemistry", 2000, pp. 6103-6105, vol. 48, No. 12, Publisher: American Chemical Society, Published in: http://pubs.acs.org/doi/abs/10.1021/0009910?prevSearch=Douillet-Breuil&searchHistoryKey=.
Stephen M. Boue et al., "Phytoalexin-Enriched Functional Foods", "Journal of Agricultural and Food Chemistry", 2009, pp. 2614-2622, vol. 57, Publisher: American Chemical Society, Published in: http://pubs.acs.org/doi/pdf/10.1021/jf8040403.
Anita M. Brinker and David S. Seigler, "Time Course of Piceatannol Accumulation in Resistant and Susceptible Sugarcane Stalks After Inoculation With . . . ", "Physiological and Molecular Plant Pathology", 1993, pp. 169-176, vol. 42, No. 3, Publisher: Elsevier, Published in: ww.sciencedirect.com/science/article/pii/S0885576583710155.
Anne-Celine Douillet-Breuil et al., "Changes in the Phytoalexin Content of Various *Vitis* Spp. In Response to Ultraviolet C Elicitation", "Journal of Agricultural and Food Chemistry", 1999, pp. 4456-4461, vol. 47, Publisher: American Chemical Society, Published in: http://pubs.acs.org/doi/abs/10.1021/9900478?prevSearch=Phytoalexin%2Bcontent%2Bof%2Bvarioue/02Bvitis%2BSpp.&searchHistoryKey=.
ISA/US, "International Search Report and Written Opinion for the corresponding PCT application US2013/023510", Apr. 15, 2013.
R. Ruggiero et al., "Photodegradation of sugar cane bagasse acidolysis lignins", "Journal of Photochemistry and Photobiology A: Chemistry", 2005, pp. 150-155, vol. 173, Publisher: Elsevier, Published in: http://www.sciencedirect.com/science/article/pii/S1010603005000201.
Christine K. Y. Yu et al., "Constitutive Accumulation of cis-piceid in Transgenic Arabidopsis Overexpressing a Sorghum Stilbene Synthese Gene", "Plant and Cell Physiology", 2006, pp. 1017-1021, vol. 47, No. 7, Publisher: Oxford University Press, Published in: http://pcp.oxfordjournals.org/content/47/7/1017.full.pdf+html.

*Primary Examiner* — Brian J Davis
(74) *Attorney, Agent, or Firm* — Eugene J. Molinelli; Beusse Wolter Sanks & Maire PLLC

(57) ABSTRACT

It has been discovered that irradiating the cut side of sugarcane billets, preferably 2-50 mm, with UVB or UVC light or combinations thereof initiates stilbene production, particularly resveratrol and piceatannol. In an embodiment the cut sides of sugarcane billets of a predetermined thickness are irradiated with Ultraviolet-C or Ultraviolet-B light or combinations thereof at an intensity and for a duration of time sufficient to produce a significant increase in a level of one or more stilbenes in the irradiated billets compared to a level of stilbenes in billets that are not irradiated; and the irradiated sugarcane billets are maintained for at least about three days up to about 20 days, to optimize stilbene levels.

26 Claims, 9 Drawing Sheets

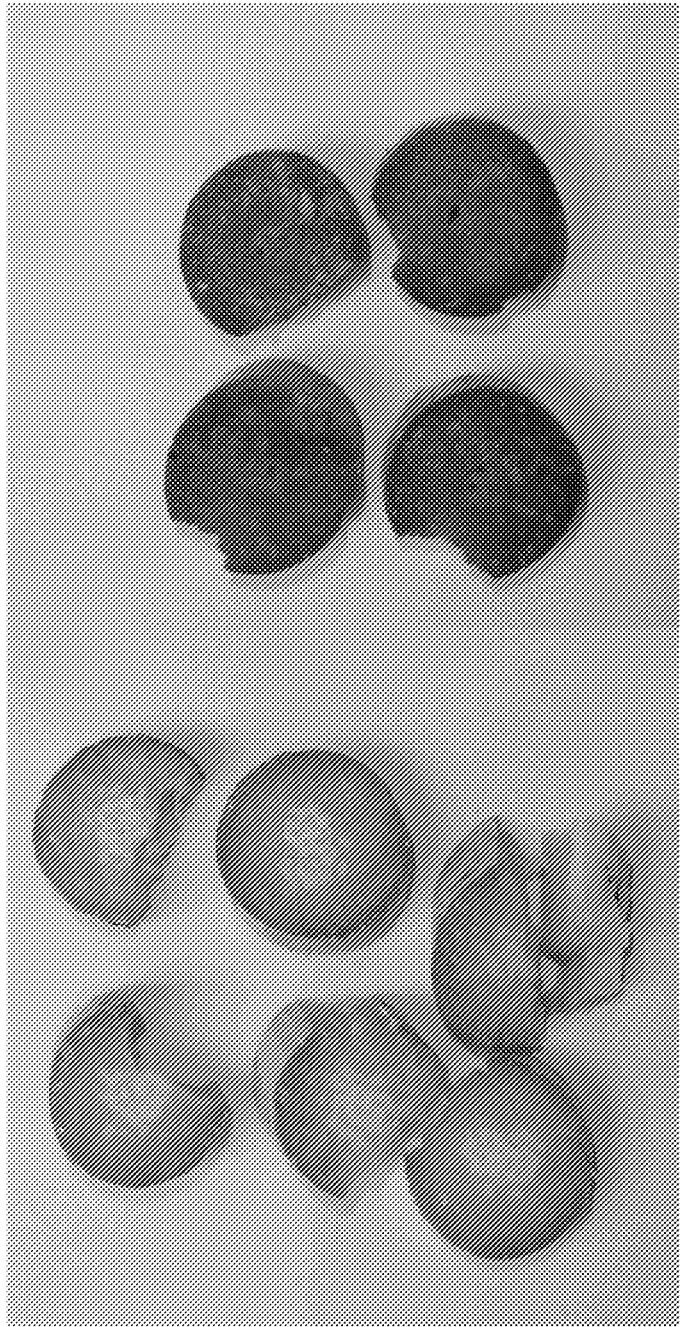

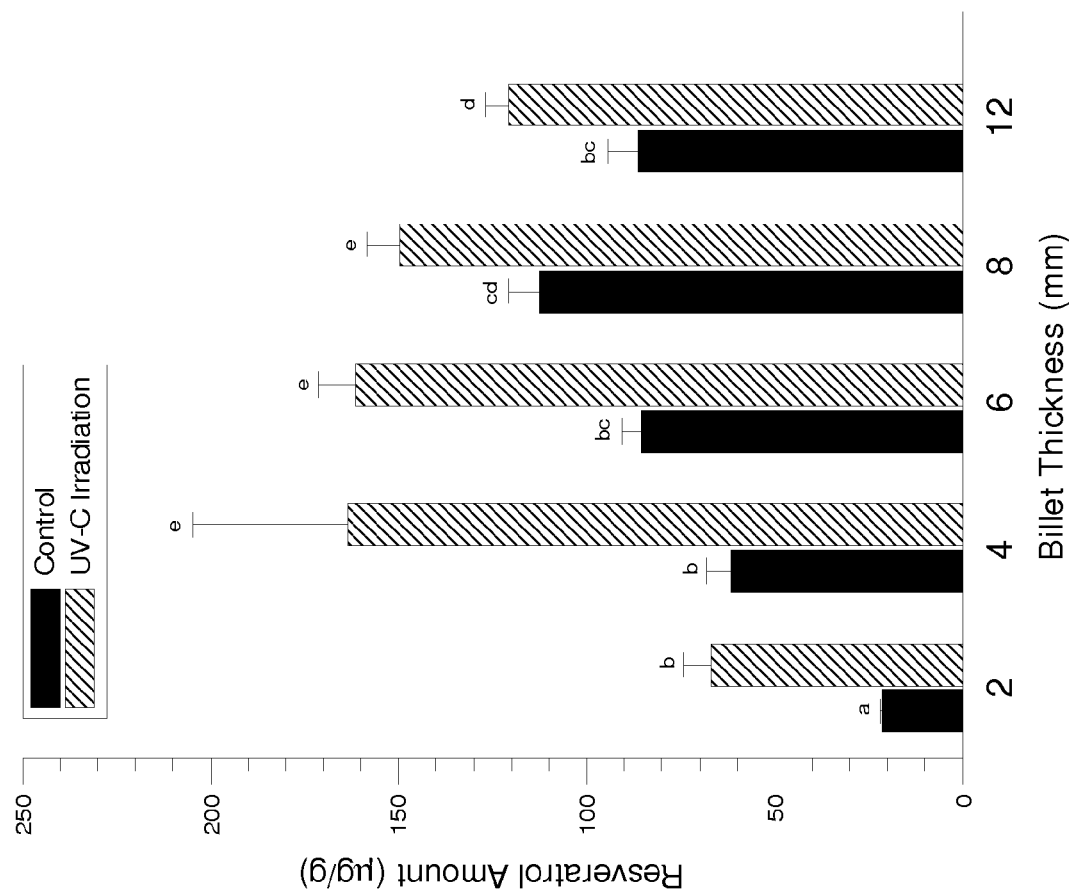

POSTHARVEST PRODUCTION AND ENHANCEMENT OF RESVERATROL AND PICEATANNOL IN SUGARCANE

CROSS-REFERENCES TO RELATED APPLICATIONS

This application claims the benefit of Provisional Application No. 61/591,724, filed on Jan. 27, 2012, and international application no. PCT/US 13/23510, filed on Jan. 28, 2013, the entire contents of which are hereby incorporated by reference as if fully set forth herein, under 35 U.S.C. §119(e).

STATEMENT REGARDING FEDERALLY SPONSORED RESEARCH

This invention was made with government support under Contract Nos: 6435-53000-002-00D and 6435-53000-002-03G awarded by the United States Department of Agriculture. The government has certain rights in the invention.

FIELD OF THE INVENTION

The present invention relates to a method of postharvest production and enhancement of resveratrol and piceatannol in sugarcane, and a method of producing sugarcane fiber with enhanced levels of stilbenes.

BACKGROUND OF INVENTION

Beneficial health effects associated with the consumption of dietary fruits and vegetables and free radicals especially have been associated with reducing the risk of various diseases including cardiovascular disease, cancer, atherosclerosis and other age-related diseases induced. Phenolic compounds are the most abundant hydrophilic antioxidants in the diet and the most active antioxidant compounds. Nijveldt R J, et al., *Am J Clin Nutr* 74:418-426 (2001). Hodgson J M, *J Sci Food Agric* 86:2492-2498 (2006). Erlejman A G, *Free Radic Biol. Med* 41:1247-1256 (2006). Moon Y J, *Toxicol Vitro* 20:187-210, (2006). Stangl V, *Mol Nutr Food Res* 50:218-228 (2006). Dudonn'e S, *J Agric Food Chem* 57:1768-4774 (2009). Jacobo-Vel'azquez D *J Food Sci* 74:R107-R113 (2009). The balance between antioxidation and oxidation is essential for maintaining health.

Stilbenes are a type of phenolic compound that include trans-piceatannol and trans-resveratrol (hereafter "piceatannol" and "resveratrol," respectively). Stilbenes in general, and resveratrol in particular, have beneficial biological properties that include antibacterial and antifungal effects, as well as cardioprotective, anti-inflammatory, neuroprotective and anticancer actions. Resveratrol also has positive effects on longevity and age-related deterioration. Piceatannol and viniferins are other phenolic compounds that are usually found in lower concentrations than resveratrol in grapes and, as a result, their bioactivity has been studied less than that of resveratrol; nevertheless, some of their health-promoting properties including anticancer properties have been investigated. Raúl F. Guerrero et al; Innovative Food Science and Emerging Technologies 11 (2010) 231-238. Research has linked the antitumor activities of piceatannol to its ability to inhibit cell proliferation and arrest cells in the S phase. When compared to resveratrol, piceatannol is a stronger antioxidant and inducer of apoptosis.

Resveratrol is found in many different plants in significant quantities, including grapes, Japanese knotweed, peanuts, cocoa, strawberries, and *Vaccinium* berries; it is also found in red wine. Resveratrol became important in diets when examined in association with the so-called "French Paradox". A diet high in fats but also high in red wine consumption results in a lower incidence of cardiovascular disease. The main component of red wine attributed to this benefit has been resveratrol.

Piceatannol is found in only a limited number of natural sources and at low levels. Piceatannol was first isolated as an antileukemic agent from the seeds of *Euphorbia lagascae*, and is also present in grape and *Vaccinium* berries. Other plants, such as *Rheum* spp., *Machura pomifera*, and *Senna* spp., have also been reported to contain piceatannol in very low concentrations. Due to the low levels of these stilbenes and their many health beneficial properties, new sources of the resveratrol and piceatannol are important. Of particular interest are methods of processing and methods of enhancing levels of these natural stilbene compounds in existing plants that would have beneficial uses in supplements, foods, and beverages.

SUMMARY OF THE INVENTION

While certain novel features of this invention shown and described below are pointed out in the annexed claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention. No feature of the invention is critical or essential unless it is expressly stated as being "critical" or "essential."

It has been discovered that irradiating the cut side of sugarcane billets, preferably 2-50 mm, with UVB or UVC light or combinations thereof initiates stilbene production. In an embodiment a method, comprises a) providing sugarcane billets of a predetermined thickness, b) irradiating the cut side of sugarcane billets with Ultraviolet-C or Ultraviolet-B light or combinations thereof at an intensity and for a duration of time sufficient to produce a significant increase in a level of one or more stilbenes in the irradiated billets compared to a level of stilbenes in billets that are not irradiated; c) maintaining the irradiated sugarcane billets for at least about three days up to about 20 days, and d) selecting the irradiated sugarcane billets. Optimal stilbenes are obtained after about 7 days after irradiation, up to about 20 days after irradiation. In an embodiment the billets are maintained in step c) at a level of light that does not cause stilbene isomerization. In another embodiment sugarcane leaves are irradiated to produce stilbenes.

The intensity of UVB light ranges from about 10 mW/cm2 to about 50 W/cm2 and the intensity of UVC light ranges from about 1 mW/cm2 to about 25 mW/cm2. Irradiation lasts from about 10 minutes to about 3 hours. The predominant stilbenes are resveratrol and piceatannol.

In an embodiment the temperature during step b) is maintained at a temperature of from about 20 degrees Centigrade to about 40 degrees Centigrade. In another embodiment tithe temperature during step c) is maintained from about zero degrees Centigrade and to about 40 degrees Centigrade. In another embodiment the stilbenes are extracted from irradiated billets after step c.

In an embodiment the sugarcane billets in step a) are obtained from sugarcane that was inoculated with a fungus that increases stilbene production in the sugarcane, such as

*Collectotrichum falcatum* or *Aspergillus sojae*. This embodiment is based on reports that these fungi cause stilbene production.

An embodiment is directed to sugarcane made by the method according to claim 1. Another embodiment is directed to sugarcane (regardless of how it is made) comprising significant levels of stilbenes, for example wherein the stilbene is resveratrol ranging from about 10 µg/g to about 500 µg/g or wherein the stilbene is piceatannol ranging from 100 µg/g to 10,000 µg/g.

Other embodiments are directed to bigasse obtained from sugarcane that is high in stilbenes, either due to irradiation of cut billets or due to prolonged storage of cut billets that have not been irradiated up to between about 3 and 20 days under conditions that do not isomerize resveratrol, preferably darkness.

BRIEF DESCRIPTION OF DRAWINGS

FIG. 2 shows a photograph of cut sugarcane billets at 24 hours after cutting and on day 7 after cutting. The degree of shading indicates that the color of the billets changes from colorless to dark red.

FIG. 6A-FIG. 6B shows the effects of size reduction on the production of A) piceatannol and B) resveratrol at day 7 with and without UVC.

DETAILED DESCRIPTION OF THE INVENTION

Figure 1B:
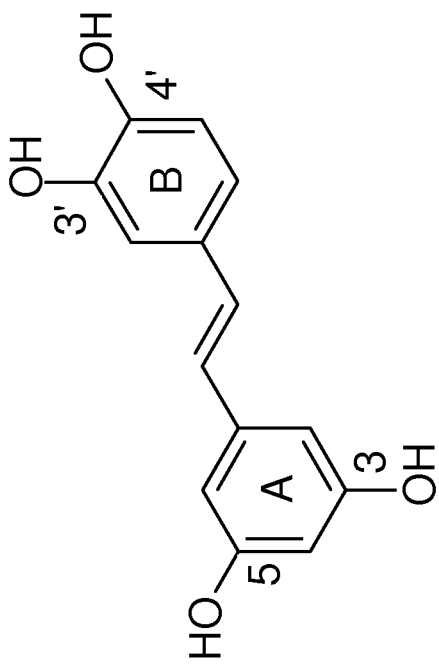
FIG. 1 shows the structure of the stilbenes trans-resveratrol and trans-piceatannol (hereafter "resveratrol" and "piceatannol," respectively).

Detailed descriptions of one or more embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

It has been discovered that irradiating a cut surface of sugarcane using ultraviolet (UV)-C (100-280 nanometer, nm, wavelengths) or UVB (280-315 nm wavelengths) light or a combination thereof for certain various durations of time and at certain various intensities dramatically increases the level of stilbenes, including resveratrol and piceatannol, compared to non-irradiated plant material. The stilbene levels increase upon incubation after irradiation, and thus should be maintained for at least about 3 days after irradiation up to about 9 to 20 days after irradiation, preferably in light levels that do not cause stilbene isomerization and at temperatures typically ranging from between about zero degrees Centigrade to about 40 degrees Centigrade. It is necessary that the UV light be applied to a cut surface.

Overview

Plant cells typically respond to environmental stimuli or abiotic stress by synthesizing secondary metabolites including phenolic compounds such as the stilbenes resveratrol and piceatannol that may protect them against the causal agent. Stilbenes are therefore considered phytoalexins that are synthesized de novo. Phytoalexins are generally antifungal and produced in plants after insect attack, wounding, or fungal infection.

Ultraviolet light has been reported to be an abiotic stress that induces an increase in phenolic compounds. UVB has been the most frequently used source of irradiation for increasing phenol antioxidant production in plants. The UVB spectral band (280-315 nm) contributes less than 2% of the short-wave photons in sunlight. UVB radiation has lower energy and is less harmful to living tissues than UVC radiation. UVC light is a germicidal non-ionizing radiation, with wavelength range from 100 to 280 nm, which has been widely studied for disinfecting fresh fruits and vegetables and for preserving their quality. Bintsis, T., et al., Journal of the Science of Food Agriculture, 80, 637-645.

Postharvest applications of UVB irradiation to fruits and vegetables (tomato, blackcurrant, blueberry, pak Choi, green lettuce, carrots and red lettuce) can enhance total soluble phenolics of the treated produce, in some cases without adversely affecting quality. Liu C, Postharv Biol Technol 59:232-237 (2011); Huyskens-Keil S, J Appl Bot Food Qual 81:140-144 (2007); Eichholz I, Food Chem 126:60-64 (2011); Harbaum-Piayda B, Postharv Biol Technol 56:202-208 (2010); and Tsormpatsidis E, Ann Appl Biol 156:357-366 (2010). Antioxidant capacity directly correlating with phenolic levels increased significantly (1.4-6.6-fold) in UVB irradiated carrots. R. J. Avena-Bustillos, et al. J Sci Food Agric 2012; 92: 2341-2348. In other studies, postharvest treatments of grape skins with UVC and UVB light produced a large increase in resveratrol derivatives (3- and 2-fold, respectively). However, others report that UV irradiation of grape skins induces resveratrol degradation. Emma Cantos, et al. J. Agric. Food Chem. 2000, 48, 4606-4612.

Phenolic compounds include stilbenes, falvonols, anthocyanins, and hydroxycinnamics. Resveratrol (3,5,4'-trihydroxy-trans-stilbene) is a low molecular weight phenolic stilbene compound occurring in a number of plant species, for which grapes are presently the most important source. Grapevine stilbenes include many compounds such as trans- and cis-resveratrol, their glucosides (5,4'-dihidroxystilbene 3-O-β-glucosides, known as piceids) (Romero-Perez, Lamuela-Raventos, Andres-Lacueva, & de la Torre-Boronat, 2001), viniferins (resveratrol dimers and trimers) (Sarig, Zutkhi, Manjauze, Lisker, & Ben-Arie, 1997), and piceatannol (3,3', 4,5'-tetrahydroxystilbene) (Cantos, Espin, & Tomas-Barberan, 2002). Piceatannol (3,4,3',5'-tetrahydroxy-trans-stilbene) is a metabolite of resveratrol by the enzyme CYP1B1 in cytochrome P450 family, with a polyhydroxystilbene core structure containing one additional hydroxyl group at the 3 position of the B-ring. Both piceatannol and resveratrol are synthesized as phytoalexins in response to fungal attack or other environmental stress in certain plants. Cantos, E., J. Agric. Food Chem. 2003, 51, 1208-1214.

While many plants such as grapes contain resveratrol and piceatannol, raw sugarcane harvested under normal conditions does not contain these stilbenes, nor are they found in sucrose or other food products made from sugarcane. Piceatannol has been isolated only from sugarcane (*Saccharum* sp.) infected with *Collectotrichum falcatum*, but not from healthy or wounded sugarcane. Sugarcane red rot is one of the major diseases of sugarcane and is named because of the large red lesions that develop in affected stalks. The causal agent is the fungus *C. falcatum*. However, reddening in sugarcane is a common infection response mentioned in the disease description of about half the leaf or stalk diseases in Sugar-Cane Diseases of the World. It is reported that sugarcane plants respond to fungal attack by means of hypersensitive response which often involves the accumulation of colored pigments at the infection site. Earlier release of a red compound referred to as red rot pigment in cells and intercellular spaces near invading *C. falcatum* in sugarcane showed the presence of the 3-deoxyanthocyandins luteolidin, apigeninidin, and caffeic acid ester of 5-O-apigeninidin. Under conditions of stress or *C. falcatum* infestation, piceatannol has been shown to be present only at infection sites on sugarcane stalks. Unfortunately, *C. falcatum* infection can inhibit sugarcane growth and decreases sugarcane yields. Typically, diseased plants are destroyed.

Although research has shown piceatannol to be a component of fungally infected sugarcane, direct evidence of resveratrol in sugarcane has not been reported. Biosynthesis of resveratrol is catalyzed by stilbene synthase (STS), which utilizes the same substrates as chalcone synthase, but a different cyclization mechanism is involved. Resveratrol STS enzymes were originally described in grapes and peanuts. SBSTS 1 is the first example of a monocot STS gene, isolated from sorghum. SBSTS 1 was expressed only following infection with fungal pathogens. Further research showed accumulation of cis-piceid, a glycoside of resveratrol, in transgenic *Arabidopsis* overexpressing SbSTS1. Other stilbenes, including resveratrol, piceatannol, and pinosylvin were not detected in sorghum using HPLC-UV detection.

Other compounds, including anthocyanins and flavonoids, have been detected in infected sugarcane. The anthocyanidin luteolidin, along with an undetermined glycoside of luteolidin, was identified in extracts of *C. falcatum*-infected sugarcane and is presumably responsible for the orange-red color, which appears at least 24 h before piceatannol is detected (Day 3). Other compounds detected in sugarcane after *C. falcatum* infection include apigenidin and the caffeic acid ester of 5-O-apigenidin.

Summary of Results of Experimental Embodiments

1) Even though raw sugarcane harvested under normal conditions does not contain resveratrol and piceatannol, it has now been discovered that these phenolic compounds can be naturally produced in sugarcane in response to abiotic stress induced by Ultraviolet light, particularly UVC and UVB, or combinations thereof.

2) Stilbenes are produced by the UVC- or UVB irradiated plant material; therefore, production increases as the surface area exposed to irradiation is increased. This can be accomplished by cutting the plant material into segments called "billets." Five different billet sizes were produced and tested: 2, 4, 6, 8, and 12 mm.

3) The amount of stilbenes produced in response to UVB or UVC irradiation depends on the intensity of the light and the duration of exposure. Temperature can also be varied to maximize stilbene levels—see R. J. Avena-Bustillos, et al, J Sci Food Agric 2012; 92: 2341-2348.

4) Stilbene levels increase to optimal levels several days after irradiation, with stilbene production first detectable on day 4. Resveratrol levels peaked at day 7 and piceatannol reached a peak level at about 8 days.

5.) Isomerization of resveratrol and piceatannol can be minimized or eliminated by maintaining the sugarcane billets in darkness or low light or in a room with fluorescent lights equipped with UV-absorbing shields.

Embodiments of the present invention satisfy a need for obtaining a food that has high levels of the important naturally produced stilbenes, piceatannol and resveratrol, without alcohol.

In one embodiment, the stilbenes produced in UV-irradiated sugarcane are extracted from irradiated plant material, or from leftover raw material or sugarcane fiber after sugarcane processing.

Certain embodiments of the invention are directed to a method for producing stilbenes, particularly resveratrol and piceatannol, in sugarcane by irradiating the sugarcane stalks or sugarcane leaves with UVC or UVt-B light or combinations thereof at an intensity and for a duration of time sufficient to produce a significant increase in a level of one or more stilbenes in the irradiated billets compared to a level of stilbenes in billets that are not irradiated.

Any variety of sugarcane can be used in various embodiments of the invention, including varieties of cv L 97-128, cv HO95 and cv LCP. Not only can the stalk be irradiated to increase stilbene production, but the leaves can also be irradiated in some embodiments. The time between harvesting and cutting, and between cutting and irradiation should be as short as possible or practical to promote freshness of the plant material, and the plant material is optimally maintained under low lighting conditions that minimize or eliminate isomerization of stilbenes.

In certain embodiments, the cut surface of sugarcane billets is irradiated with UVB or UVC light or both. UVB light ranges from about 10 mW/cm2 to about 50 mW/cm2; UVC light ranges from about 1 mW/cm2 to about 25 mW/cm2. Routine experimentation will show whether this range can be broadened. In the herein described experimental embodiments, UVC treatments using an intensity of 180 $\mu$W/cm$^2$ for 1 hour (30 min on each side of billet) at room temperature were applied. Irradiation durations depend on the UV intensity and in certain embodiments will range from about 10 minutes to about 3 hours, with preferred durations between 30 minutes and 1 hour. The durations and intensities can be determined using routine skill in the art and will vary depending on the commercial set up for handling large quantities of plant material. In certain embodiments irradiation is conducted at temperatures ranging from about 20-40 degrees Centigrade. In other embodiments, irradiated billets are then stored for at least 3 days, up to about 9 days or 20 days at temperatures ranging from about zero degrees to about 40 degrees Centigrade in darkness or low light conditions that do not permit stilbene isomerization.

Because stilbenes are produced on the irradiated plant surface, cutting the sugarcane into thin billets increases stilbene yield per pound of plant material. Any thickness can be used, for example ranging from about 2 millimeters, mm, to about 12 mm and up to about 50 mm in thickness.

In some embodiments, the method, further comprises extracting one or more stilbenes from the irradiated billets, typically in the trans form.

In some embodiments, ozone produced by cleavage of oxygen molecules of air exposed to UV light are vented. Surface temperature of the plant material is monitored, in some embodiments, for example, using an infrared thermometer (such as a Fluke Mod. 65, Fluke Corp., Tokyo, Japan). Moisture content of the plant material is monitored in some embodiments, for example, using an AACC method 44-15A.

In some embodiments, the sugarcane billets are obtained from sugarcane that was inoculated with a fungus that increases stilbene production in the sugarcane, such as *Collectotrichum falcatum* or *Aspergillus sojae*.

Other embodiments are directed to UVC- or UVB irradiated sugarcane comprising resveratrol or piceatannol in an amount that is significantly elevated compared to non-irradiated sugarcane. By significantly elevated is meant an increase of at least about 10% in irradiated sugarcane compared to controls.

Discussion

Sugarcane is processed primarily as a source of sucrose used by consumers throughout the world. Whereas some plants contain stilbenes, raw sugarcane harvested under normal conditions does not. By contrast, grapes have both resveratrol and piceatannol under normal conditions, and irradiation enhances the levels of these stilbenes. Thus, it was not certain that irradiation with UVB or UVC would produce significant levels of stilbenes in sugarcane, given that these compounds are undetected in non-irradiated sugarcane plant material. The results presented here show that the stilbenes piceatannol and resveratrol can be produced naturally in post-harvest cut sugarcane by irradiating with UVC or UVB. The present experiments represent the first time the occurrence of resveratrol in sugarcane has ever been detected.

Postharvest production of stilbenes in irradiated cut sugarcane requires an incubation of at least about 3 to 4 days, preferably under conditions that prevent stilbene isomerization, before low levels of these stilbenes can be detected. Longer incubation times of between about eight to nine days following irradiation are advantageous for production of optimal levels of stilbenes. The concentrations of the stilbenes in UVC-irradiated sugarcane are high when compared to other foods: 3184 micrograms of piceatannol per gram of material ($\mu g/g$) was obtained in UVC treated sugarcane extracts at Day 7 using an 8 mm billet size, and resveratrol was (163.5 $\mu g/g$) in UVC treated extracts at Day 7 using a 4 mm billet size. By contrast, UVC irradiation induced resveratrol levels of only (65 mg/kg) in grapes. Cantos, E. et al, *J. Agric. Food Chem.* 2000, 48, 4606-4612.

Optimization of sugarcane billet size in various embodiments also aided in increasing stilbene levels. The highest levels of stilbenes were detected in billets cut to between about 6 mm to about 8 mm after a post-irradiation incubation period of about 7 days. The levels of piceatannol were highest (2.4 mg/g and 2.3 mg/g) at 6 mm and 8 mm billet sizes, respectively, after a post-irradiation incubation period of about 7 days. Levels of resveratrol were highest (0.11 mg/g) at 8 mm billet size after about 7 days.

In the past, the difficulty of trying to tap the antioxidant and antimutagenic benefits of stilbenes has been that they are primarily phytoalexins, and are therefore often only found in infected or wounded plants and not found in healthy plants, even if the gene is present naturally in the plant. Thus, although grapes, for example, have stilbene synthase (STS) genes and active STS enzymes, consumers typically do not benefit from consuming grapes, because resveratrol is found only at low levels in healthy grapes. There is therefore a need to produce plants that contain a high and constitutive level of one or more of the desired stilbenes, or develop post-harvest methods to induce higher levels of health-promoting stilbenes.

The identification of resveratrol and piceatannol in sugarcane in this study point to the production of a new stilbene-enriched subclass of health-promoting functional food engineered post-harvest to produce increased levels of health promoting compounds that can be readily incorporated into food products. In earlier work, we introduced the concept of phytoalexin-enriched functional foods. Sugarcane containing enhanced levels of piceatannol and resveratrol may be processed into sugar or sugarcane juice, which would contain piceatannol and resveratrol. This stilbene-enhanced sugarcane or sugarcane juice may be used as a supplement or ingredient in food and beverage products, in various embodiments, to enable consumers to access the health-promoting benefits of stilbenes without the consumption of alcohol. Stilbene production may be induced in other parts of the sugarcane plant, including the leaves, in various embodiments. Food-grade fungi such as *Aspergillus sojae* and c FXX may be used to enhance stilbene production in sugarcane plants in addition to UVB and UVC irradiation.

It is also contemplated that, in some embodiments, sugarcane containing enhanced levels of piceatannol and resveratrol may be processed into sugar. The leftover sugarcane fiber or "bagasse" could then be processed and utilized as a dietary fiber supplement or ingredient in food and beverage products to enable consumers to access the health-promoting benefits of stilbenes in many different food and beverage products. The sugarcane fiber may also be processed to extract the stilbenes themselves for use as supplements or ingredients in food or beverage products or medicines. Stilbene-containing sugarcane fiber may be produced from pressing sugarcane to remove the juice, then milling the pressed sugarcane into a fiber. Preliminary results demonstrate that this type of stilbene-containing fiber may be comprised of mostly insoluble dietary fiber (~78%) and very little soluble dietary fiber (~1.6%). Stilbene-containing dietary fiber may be used as a supplement or an ingredient in food and beverage products to enable consumers to access the health-promoting benefits of stilbenes in many different food and beverage products.

Additionally, sugarcane is now used in many methods of manufacturing biofuels. The bagasse irradiated sugarcane can also be further processed to allow the discarded material to be used in biofuels production.

Various embodiments of the present invention produce several advantages over current state of the art. In some embodiments, high levels of stilbenes are produced and marketed in combination with sugar (sucrose), and certain sugar products from irradiated sugarcane. In some embodiments, the stilbenes are extracted at the same time as the generation of sucrose takes place, and marketed separately.

UV Ranges

Any method known in the art can be used for exposing sugarcane plant material (hereafter "plant material") to UV on a commercial scale. For example, systems can include multiple UV lamps that irradiate plant material on one or both sides as it passes by on a conveyor belt.

Examples of lamps producing UVB light include Uvitron UV Conveyor 40 dual-lamp curing system with two SunRay 400 SM UVB flood lamps and adjustable (1.5-5.0 in) lamp height (Uvitron International Inc., West Springfield, Mass., USA). UVB lamp VL-340-E (240 W) (Viber Lourmat, Marne le Valle, France) (peak output at 340 nm) equipped with three lamps of 80WT-40 M. Emma Cantos, et al. *J. Agric. Food Chem.* 2000, 48, 4606-4612.

UVC irradiation can be generated using three Sylvania germicidal lamps (G30T8) (peak output at 254 nm). UVC treatments of 30 minutes at room temperature (1780-2300 $\mu W/cm^2$) have been reported using grapes that were stored at 0° C. for 10 days and then transferred to 15° C. for 5 days to simulate the commercialization period. Emma Cantos, et al. *J. Agric. Food Chem.* 2000, 48, 4606-4612. The plant material was irradiated in a system comprising 34 UVC lamps, with 17 lamps (254 nm, Silvana, G30T8) in each of two panels positioned above and below the plant material. A theoretical power of 510 W at 42 cm was applied for 60 s [equivalent to 12,000 microW/cm$^2$] according to the protocol proposed. The average flow velocity was measured to ensure reproducibility of the process (14.72 mW/cm$^2$, using Vilber Lourmat VLX 254 radiometer). Raúl F. Guerrero et at; Innovative Food Science and Emerging Technologies 11 (2010) 231-238.

Another source of UVC light is the model TUV TL-D 30 W UVC light of maximum wavelength 254 nm (Philips, Amsterdam, The Netherlands).

If the plant material is on a conveyor belt, then the speed of the conveyor and the distance between the plant material and the UV fight sources can be adjusted so to control e duration of exposure, hence also the intensity or dose of UV.

The UV dose (energy) and peak intensity (power) can be measured using equipment known in the art including a Uvicure Pius II radiometer (Err Inc., Sterling, Va., USA).

The electromagnetic spectrum of ultraviolet light can be subdivided in a number of ways. The ISO standard on determining solar irradiances (ISO-21348) describes the following ranges:

| Name | Abbreviation | Wavelength range (in nanometers) | Energy per photon (in electronvolts) |
|---|---|---|---|
| Ultraviolet | UV | 400-100 nm | 3.10-12.4 eV |
| Ultraviolet A | UV-A | 400-315 nm | 3.10-3.94 eV |
| Ultraviolet B | UVB | 315-280 nm | 3.94-4.43 eV |
| Ultraviolet C | UVC | 280-100 nm | 4.43-12.4 eV |
| Near Ultraviolet | NUV | 400-300 nm | 3.10-4.13 eV |
| Middle Ultraviolet | MUV | 300-200 nm | 4.13-6.20 eV |
| Far Ultraviolet | FUV | 200-122 nm | 6.20-10.16 eV |
| Hydrogen Lyman-alpha | H Lyman-$\alpha$ | 122-121 nm | 10.16-10.25 eV |
| Extreme Ultraviolet | EUV | 121-10 nm | 10.25-124 eV |
| Vacuum Ultraviolet | VUV | 200-10 nm | 6.20-124 eV |

EXAMPLES

Example 1

Materials and Methods

Preparation of Sugarcane and Extraction of Stilbenes

Sugarcane (*Saccharum* sp. L.) plants (cv L 97-128) were grown at the U.S. department of Agriculture, Agricultural Research Service, Southern Regional Research Center in New Orleans, La., and harvested at 6 months from planting. L97-128 is also a "Ratoon" variety meaning it can be cut and root material left in the ground to be grown another year. After 3-4 years the sucrose content decreases so stalks are then typically cut into long billets and replanted to start the Ratoon process over. The UVC data for cv L 97-128 was from 1st "Ratoon" meaning 1 year after initial planting. There may be differences in stilbene production at different "Ratoons" or years after initial planting.

Experiments were conducted using freshly harvested sugarcane of the variety cv L 97-128. Cultivars cv HO95 and cv LCP were only tested for stilbene production as controls. The lower three foot section of the sugarcane stalk was used for uniformity. Other sections of the sugarcane can also be used, including sugarcane leaves. A 10% solution of Clorox™ from the Clorox Co. of Oakland, Calif. was used for surface sterilization.

Authentic standards of trans-piceatannol (Alexis Biochemicals, San Diego, Calif.) and trans-resveratrol (Sigma, St Louis, Mo.) were purchased. HPLC grade solvents acetonitrile and methanol were purchased (JT Baker, Phillipsburg, N.J.). Water was obtained using a Millipore system and used during sample preparation procedures and HPLC analyses.

Sugarcane billets were cut to thicknesses of 12 mm using pruning shears, or to thicknesses of 2, 4, 6, 8, and 12 mm using a Rockwell RK7240.1 10-Inch Table Saw.

Harvesting, cutting, and extraction of stalk billet samples were carried out in low light or in a room with fluorescent lights equipped with UV-absorbing shields, to prevent isomerization of stilbenes. Isomers can be detected during HPLC characterization because isomers elute at different retention time and give a characteristic UV absorption pattern. No isomers were detected in the experiments described herein. Six to eight billets were harvested at each time point to minimize variability.

Lyophilized billets were ground in a Tekmar A10 analytical mill (Janke and Kunkel GmbH & Co., Staufen, Germany). Samples (0.2 g) were extracted using 2 mL methanol with sonication for 1 hour. Methanol extracts were filtered using 0.45 μm filters and analyzed by HPLC. A person of skill in the art would be able to vary the methods as needed; lyophilization is not required.

Phytoalexin Isolation and Identification

Figure 1A:
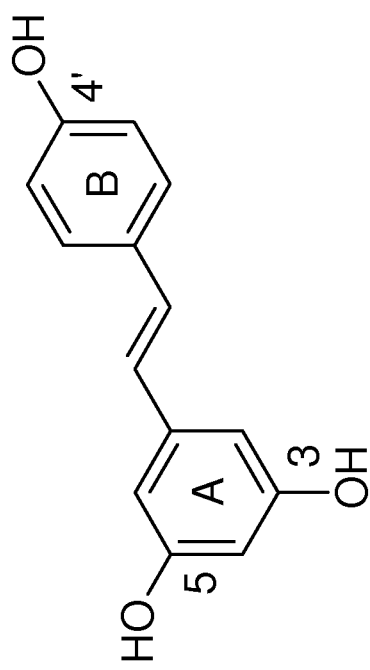

Piceatannol and resveratrol were isolated using techniques developed at the Southern Regional Research Center (ARS, USDA, New Orleans, La.). For the isolation of the phytoalexins, semi-preparative HPLC was utilized, however any method known in the art can be used. The column was a Whatman ODS-2 10 mm×500 mm using a flow rate of 3.0 ml/min with the following solvent system: A=acetonitrile, B=water; 5% A for 15 min, then 5% A to 90% A in 40 min followed by holding at 90% A for 20 min. Piceatannol and resveratrol as shown in FIG. 1 were confirmed by UV-VIS spectrophotometry, APCI mass spectrometry (MS and MS/MS), and NMR ($^1$H and $^{13}$C) analyses. $^1$H and $^{13}$C spectra were recorded in deuterated acetone with a Bruker DMX-500 spectrometer (Billerica, Mass.).

For the identification of stilbenes, the LC-MS/MS analyses were performed in negative ionization mode on an LCQ ion trap mass spectrometer (Thermo Finnigan, San Jose, Calif.) fitted with an atmospheric pressure chemical ionization (APCI) probe. The ion trap was connected to a Waters 600E Series HPLC instrument consisting of a Waters 717 autosampler, and Waters 996 UV-Vis photodiode array detector. APCI conditions were optimized using piceatannol as a standard. The full APCI-MS spectrum of crude methanol extract was first obtained followed by the collision-induced dissociation (CID) spectra of select ions. HPLC effluent at 1 ml/min was introduced directly into the interface without splitting using a source temperature of 500° C. and the capillary temperature was 220° C. The sheath gas flow was set to 60 arbitrary units. The full scan mass spectra of the stilbenes from m/z 100-1000 were measured using 500 ms for collection time and three micro scans were summed. Tandem mass spectrometry was performed using a collision energy of 35% for MS-MS analyses.

Analysis of Resveratrol and Piceatannol

The quantity of piceatannol and resveratrol in sugarcane billets was determined by HPLC analysis. All analyses were performed using a Waters (Milford, Mass.) system with a W717 sample injector, a W600E pump, and a W996 photodiode array detector (PDA). Stilbenes were separated using a Luna (Phenomenex, Torrance, Calif.) $C_{18}$ reverse-phase column (250×4.6 mm, 5 μm particle size). A guard column containing the same packing was used to protect the analytical column. The injection volume of sample was 10 μL with a flow rate of 1.0 ml/min with the following solvent system: A=3 mM ammonium acetate/water, B=acetonitrile; 0% B to 45% B in 17 min, then 45% B to 90% B in 10 min followed by holding at 90% B for 6 min. The spectra were collected between 220 and 400 nm by PDA, and stilbnenes were quantified at 306 nm for resveratrol and 325 nm for piceatannol.

To quantify the piceatannol and resveratrol contents in sugarcane, calibration curves were constructed prior to sample analysis using authentic piceatannol and resveratrol. The linear range of quantitative analyses for piceatannol was 0.025-25.0 μg/mL. The linear range of quantitative analyses for resveratrol was 0.025-20.0 μg/mL. The corresponding correlation coefficients ($R^2$) were 0.9974 and 0.9980, indicating excellent correlations between peak areas and standard concentrations.

UVC Irradiation Experimental Design

Sugarcane billets were subjected to postharvest treatments using a 3×9 factorial design. Factors studied were UV irradiation applications (UVC, and no UV application). Three replications of the 27 treatments were conducted for a total of 81 samples. Six to eight billets were harvested at each time point to minimize variability. Experiments have also been conducted using UVB light, which also increased stilbene levels in the billets and incubation times (0-9 days).

UVC irradiation was performed using a single Philips germicidal lamp (TUVF17T8) (17 W) (peak output at 254 nm). The distance between lamps and sugarcane billets was 15 cm. As described herein, other UV set ups can be used for varying the intensity of irradiation by varying the light source, the number of light sources, the duration of exposure and the intensity of the light.

UVC (180 μW/cm$^2$) treatments of 1 hour (30 min on each side of billet) at room temperature were conducted. Both irradiated and control (non-irradiated) sugarcane billets were then paced in plastic trays, covered to avoid dehydration, and incubated in darkness at 23° C. for varying periods. Minimizing exposure of the billets to light will minimize stilbene isomerization that can occur if the billets are left exposed to indoor or outdoor lighting. Samples were then stored at −80° C. for 1 day and lyophilized before analysis.

All experimental data were analyzed using XLSTAT (version 2007.6; Addinsoft, Inc., New York, N.Y.). Statistical evaluation of the results was performed by Dunnett's multiple-comparison test. The Dunnett procedure compares the means as measured for each treatment group. Differences are considered significant at $p<0.05$. Each value is presented as the mean±standard deviation (SD).

Example 2

Experimental results

Identification of Resveratrol and Piceatannol

Figure 3A:
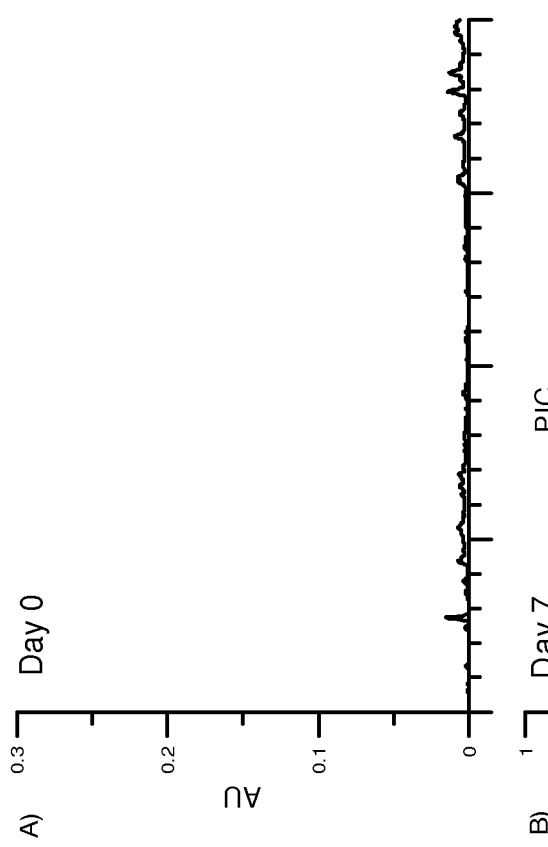
FIG. 3A-FIG. 3B shows HPLC chromatograms of cut sugarcane controls at A) day 0 and B) day 7.
Figure 3B:
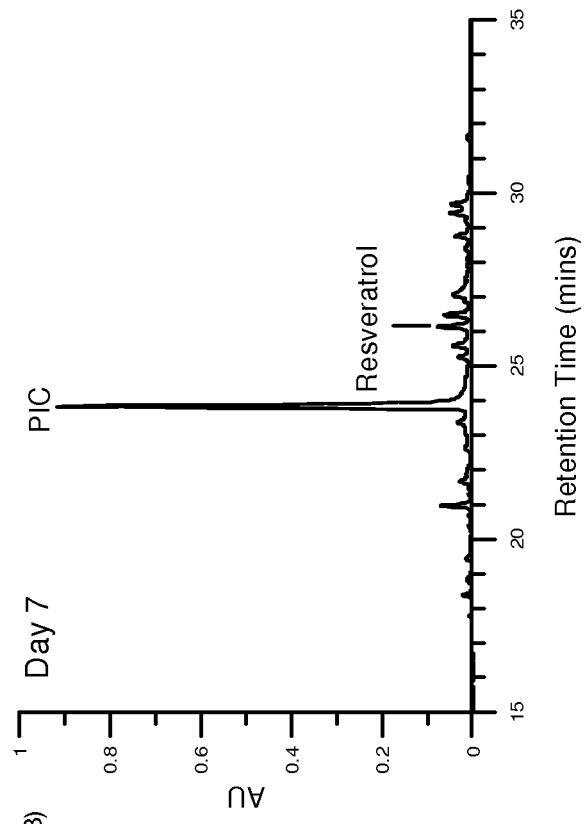

The color of the cut sugarcane changed from colorless to light red (beginning at Day 2-3) to dark red (beginning at Day 5-6). FIG. 2 displays a photograph of cut sugarcane billets at day 1 and day 7 post-UVC irradiation. HPLC analysis was conducted to determine the polyphenolic components of cut sugarcane billets. FIG. 3 displays the HPLC chromatogram of cut sugarcane at A) day 0 and B) day 7. Stilbenes were not present in sugarcane samples analyzed at day 0. Samples at day 7 contained two stilbenes with retention times of 23.9 min for piceatannol and 26.2 min for resveratrol.

Figure 4A:
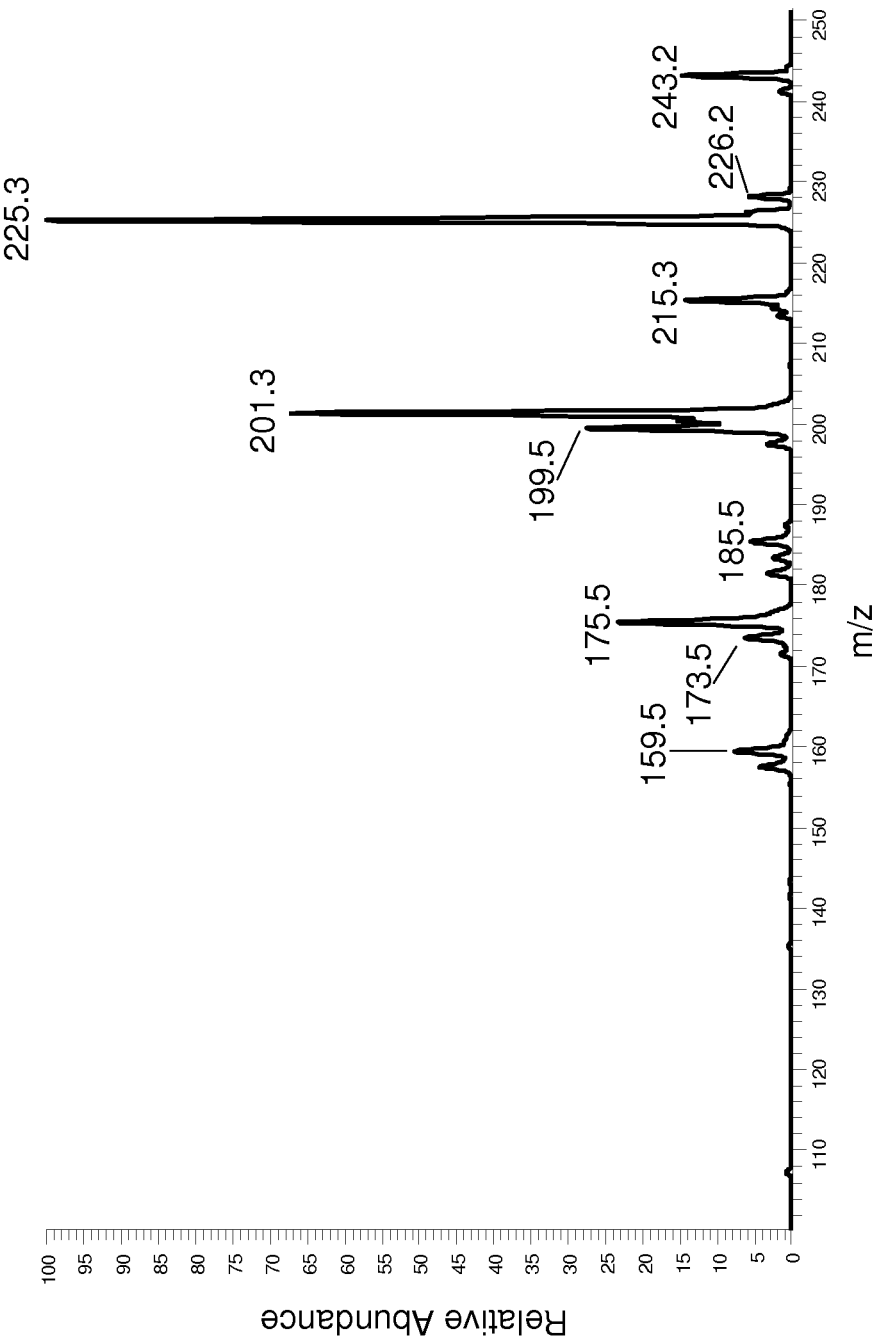
FIG. 4A-FIG. 4B shows the tandem mass spectrometry spectra of sugarcane stilbenes in A) piceatannol from cut sugarcane at day 7 and B) resveratrol from cut sugarcane at day 7.
Figure 4B:
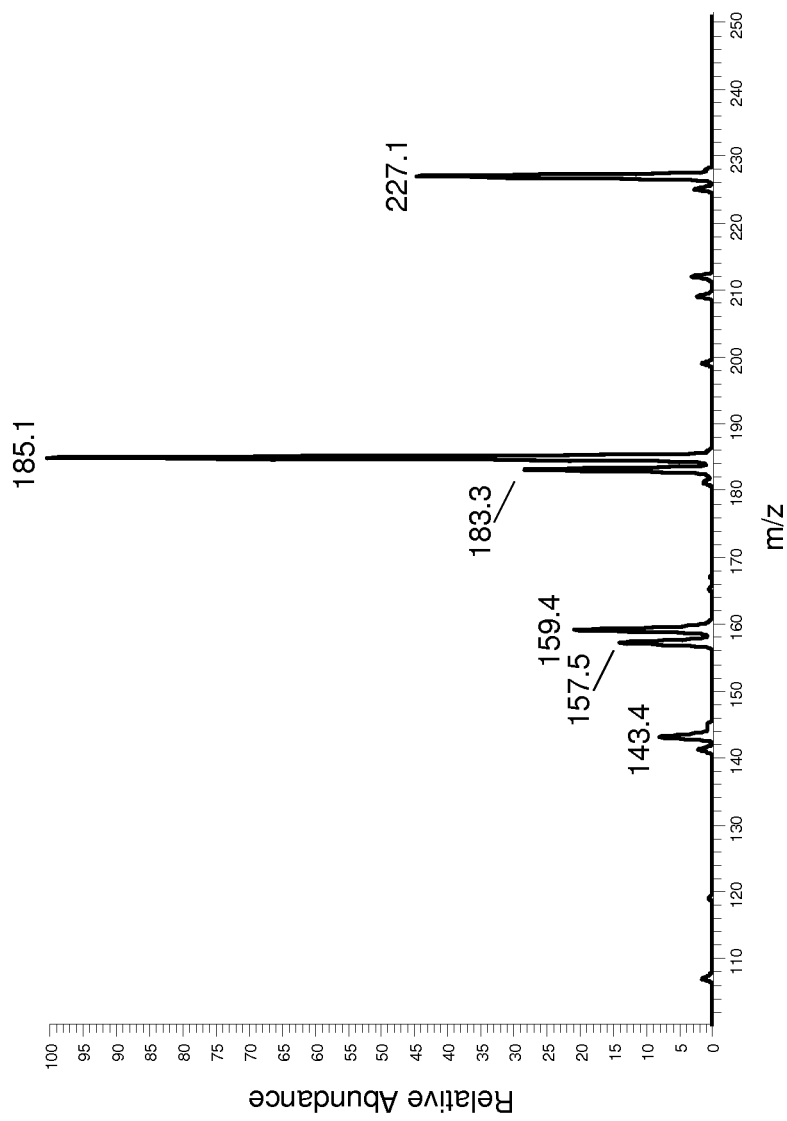

Tandem mass spectrometry was used to confirm the identity of the two stilbenes in sugarcane samples. FIG. 4 displays the MS/MS spectra of both piceatannol and resveratrol from sugarcane after an incubation period of 7 days. The MS/MS spectrum of piceatannol is shown in FIG. 4A. The ion at m/z 243 corresponds to the deprotonated [M-H]$^-$ of piceatannol. Piceatannol, which contains 3',4'-dihydroxyl groups, eliminates one molecule of $H_2O$ to produce the [M-$H_2O$]$^-$ ion at m/z 225. The ion at m/z 201 is due to neutral loss of $C_2H_2O$ from the parent ion. The MS/MS spectrum of resveratrol is reported in FIG. 4B. The spectrum contains the [M-H]$^-$ at m/z 227, which confirms the molecular weight. The two product ions at m/z 185 [M-H—$CH_2CO$]$^-$ and the ion at m/z 143 [M-H-2$CH_2CO$]$^-$ involve the sequential loss of two ketene molecules $C_2H_2O$. The MS/MS spectra of piceatannol and resveratrol were consistent with previous reports.

Piceatannol has been previously identified in sugarcane stalks infected with *Colletotrichum falcatum*, however, neither piceatannol nor resveratrol are found in raw sugarcane. Resveratrol and piceatannol were determined in sugarcane billet samples after UVC irradiation by LC-MS and MS/MS data and UV spectra. Evaluation of the retention times and UV spectra for the peaks corresponding to resveratrol and piceatannol in sugarcane extracts revealed identical spectra compared with that in standards. Also, LC-MS and LC-MS/MS data confirmed that the compound identified were resveratrol and piceatannol. The compounds identified had identical retention times and similar fragmentation patterns compared with that of resveratrol and piceatannol standards and published data. Unequivocal identification of the two stilbene structures was provided by NMR spectroscopic analysis.

Trans-piceatannol: APCI m/z 243 [M-H]$^-$; MS/MS spectrum shown in FIG. 4A; $^1$H NMR δ 6.97 (d, 1H, J=2 Hz, H6'), 6.89 (d, 1H, H-α or H-β), 6.83 (dd, 1H, $J_{2,6}$=2 Hz, $J_{5,6}$=8 Hz, H-6), H-α), 6.73 (d, 1H, J=16 Hz, H-α or H-β), 6.73 (d, 1H, J=8 Hz, H-5), 6.43 (d, 2H, J=2 Hz, H2' and H-6'), 6.15 (t, 1H, J=2 Hz, H-4'). $^{13}$C NMR δ 159.6 (C3, 5), 146.3 (C4'), 140.8 (C1), 132.9 (C1'), 129.7 (C-β), 126.9 (C-α), 119.9 (C-6'), 116.2 (C2'), 113.8 (C5'), 105.6 (C2), 102.6 (C4, 6).

Trans-resveratrol: APCI m/z 227; MS/MS spectrum as shown in FIG. 4B; $^1$H NMR δ 7.42 (d, 2H, J=8.25 Hz, H2' and H6'), 7.03 (1H, H-β), 6.99 (1H, H-α), 6.89 (d, 2H, J=8.2 Hz, H3' and H5'), 6.81 (broad signal, 1H, H2), 6.68 (br s, 1H, H6), 6.53 (2H, br s, H-2,6), 6.26 (br s, 1H, H4). $^{13}$C NMR δ 159.6 (C3, 5), 158.2 (C4'), 140.9 (C1, 5'), 130.0 (C1'), 129.1 (C-β), 128.8 (C2'), 126.9 (C-α), 116.4 (C3'), 105.7 (C2, 7, 6'), 102.7 (C4).

Production and Enhancement of Piceatannol and Resveratrol Following UVC Irradiation The time between harvesting and cutting, and between cutting and irradiation can vary. To minimize variability, all samples were irradiated with UVC (180 μW/cm2) within 30 minutes of cutting for 1 hour (30 minutes on each side of the billet). Other intensities and durations of UV irradiation can be chosen to optimize stilbene production. In all of the experiments described here, irradiated sugarcane billets were maintained in darkness for various durations of time after irradiation before being analyzed for stilbenes. The control was cut sugarcane that was left on a lab bench in low light and turned over for the same exposure time as the UVC exposure time.

Figure 5A:
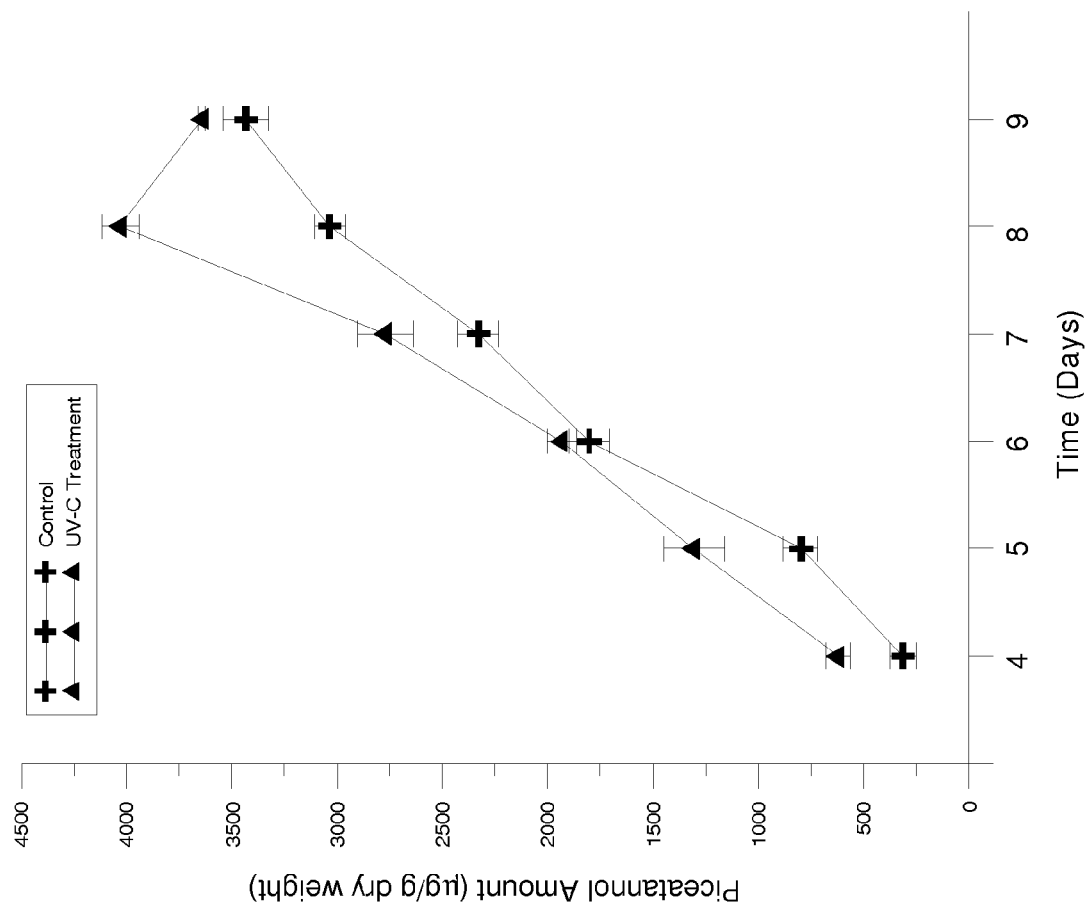
FIG. 5A-FIG. 5B shows the post-harvest production of A) piceatannol and B) resveratrol in cut sugarcane with and without UVC irradiation over a nine day period.
Figure 5B:
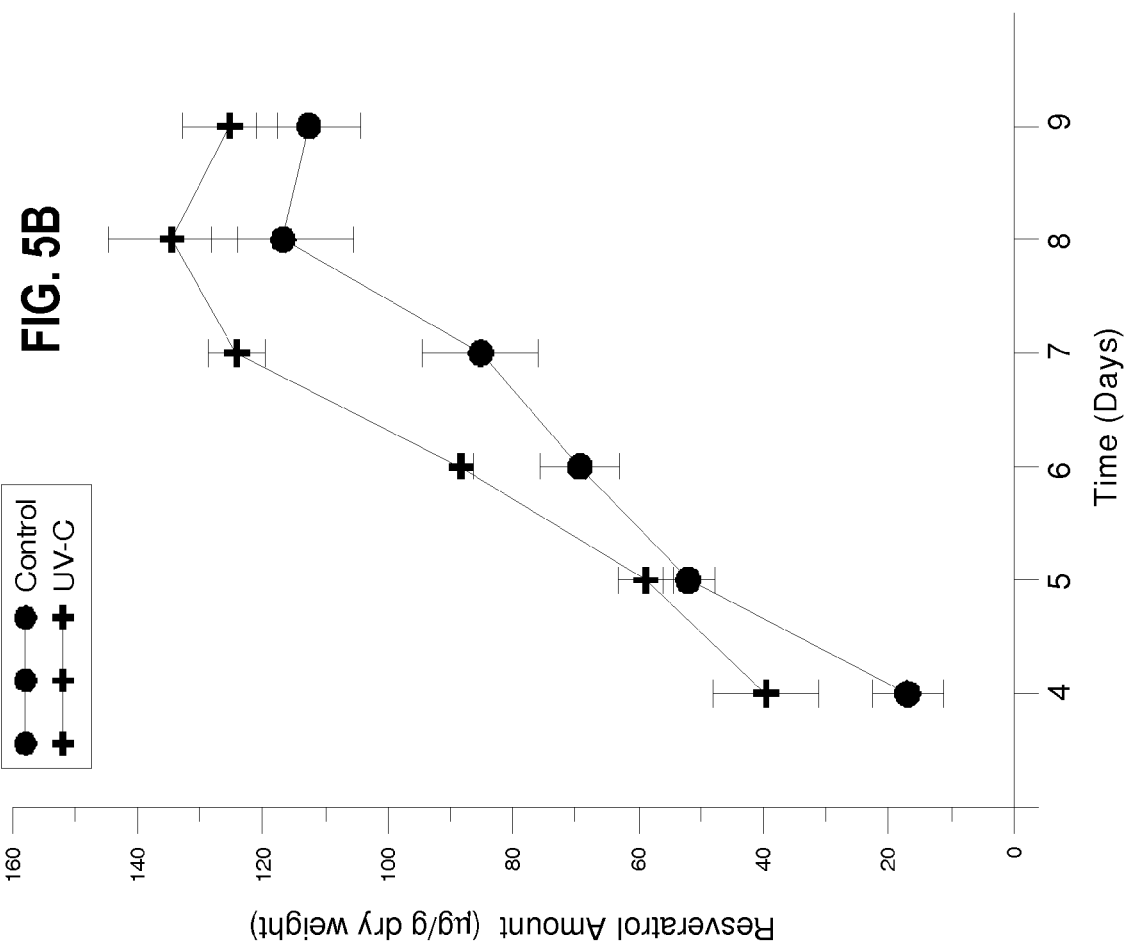

To determine the incubation time necessary to produce optimal amounts of sugarcane stilbenes, a time course experiment was conducted using sugarcane billets 12 mm thick. The post-harvest time-course induction of piceatannol (FIG. 5A) and resveratrol (FIG. 5B) after UVC irradiation for 1 hour within 30 minutes after cutting is displayed over a 9 day period. The irradiated billets and control billets were maintained in darkness until stilbene analysis took place. Both resveratrol (17.0 μg/g) and piceatannol (313.4 μg/g) were first detected in irradiated control billets at day 4. The highest level of resveratrol (116.7 μg/g) in controls was detected at Day 8. Piceatannol reached a maximum concentration (3434 μg/g) in controls at Day 9. These results show that just cutting sugarcane billets and keeping them in the dark or under conditions that do not isomerize resveratrol will lead to stilbene production. In certain embodiments, cut sugarcane is not irradiated but is maintained in darkness or under conditions that do not isomerize stilbenes, for up to about 20 days, thus producing sugargane rich in stilbenes, as is shown in the controls of this series of experiments.

The time-course induction of piceatannol after UVC irradiation (FIG. 5A) shows that increased piceatannol above control levels was detected after each day of incubation starting at day 4 (621.3 µg/g). The highest concentration of piceatannol after UVC irradiation was observed at day 8 (4029.8 µg/g). The time-course induction of resveratrol after UVC irradiation (FIG. 5B) shows increased amounts of resveratrol above control levels after each day of incubation starting at day 4 (39.6 µg/g), with maximal amounts observed at day 8 (134.5 µg/g). It is expected that by increasing the intensity of either UVB or UVC light the stilbene levels can be increased much higher. Routine experimentation will optimize the stilbene levels. It is expected that resveratrol up to about 500 µg/g and piceatannol up to about 10,000 µg/g can be obtained using UVB or UVC irradiation or combinations thereof.

Size Reduction Enhances Stilbenes

Figure 6A:
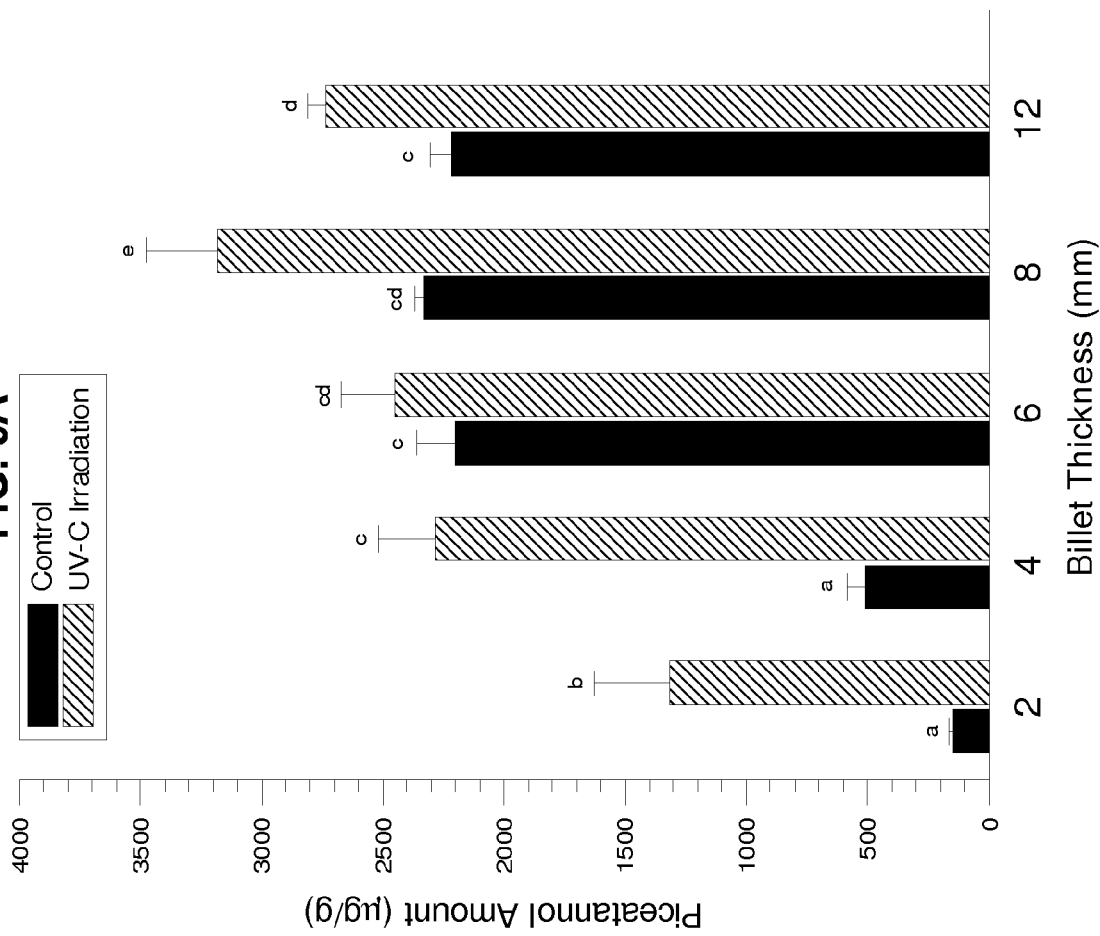

Initial experiments described above with cut sugarcane were conducted using a 12 mm billet thickness. The effect of size reduction to enhance resveratrol and piceatannol amounts is shown in FIG. 6. Cut sugarcane at different billet sizes (thickness) were similarly irradiated with UVC (180 µW/cm2) for 1 hour on day 0 and incubated for 7 days in darkness. Five different billet sizes were used in this study: 2, 4, 6, 8, and 12 mm. At a 2 mm billet size low levels of piceatannol (148 ug/g) and resveratrol (21.4 ug/g) were observed in controls. As is shown in FIG. 6A, a significant increase in piceatannol (2198 ug/g) was observed at a billet size of 6 mm. Piceatannol amount (3184 ug/g) was highest in UVC treated extracts at Day 7 using an 8 mm size. Resveratrol (163.5 ug/g) was highest in UVC treated extracts at Day 7 using a 4 mm billet size. FIG. 6B.

In the studies with UVC, stilbene quantitation was conducted on dried samples with no water present to aid in extraction of stilbenes—dry samples were ground to fine powder. Sugarcane typically contains up to 50% water and results from our lab using cut billets confirmed this water content. Fresh weight stilbene concentrations can be approximated by reducing dry weight concentrations by one half. However, the concentrations of stilbenes detected using fresh weight amounts would still be significantly higher compared to that found in many other food sources.

Example 3

UVB Irradiation

Experiments were also conducted using 12 mm billets and the same conditions described above for UVC irradiation, except that high intensity UVB irradiation (peak intensity was 310 µWatts/m$^2$ which is 31 mW/cm$^2$) was administered for a 2 min duration (1 min on each side) on Day 0. At Day 7 after irradiation the piceatannol amount in UVB samples was 2762.3 µg/g.

Two other sugarcane varieties, HO 95-988 and LCP 85-384, were only cut and incubated for 7 days (no UV treatment) in order to check control levels of stilbenes for comparison with the sugarcane variety L97-128. Stilbenes were not detected in freshly cut sugarcane samples on Day 0. HO 95-988 contained slightly higher amounts of piceatannol (80.3 µg/g) and resveratrol (11 µg/g) when compared to variety LCP 85-384 (piceatannol 45.7 µg/g, resveratrol 6 µg/g on day 7). However, the concentrations of stilbenes were significantly lower than levels detected in sugarcane variety L97-128.

Resveratrol and piceatannol are naturally occurring phenolic compounds belonging to the stilbene family. Both resveratrol and piceatannol have numerous health benefits, including cancer preventative properties, anti-inflammatory properties, prevention of atherosclerosis and coronary diseases, anti-oxidant properties and anti-leukemic properties. A new plant source, sugarcane, was used to produce significant quantities of the stilbenes piceatannol and resveratrol. Both stilbenes were identified in cut sugarcane billets after incubation for 4 days. Postharvest ultraviolet C (UVC) or ultraviolet B (UVB) treatment or combinations thereof, was used to enhance induction of stilbene biosynthesis in cut sugarcane billets and leaves.

The invention is illustrated herein by the experiments described above, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

What is claimed is:

1. A method, comprising
    a) providing sugarcane billets of a predetermined thickness;
    b) irradiating the cut side of sugarcane billets with Ultraviolet-C or Ultraviolet-B light or combinations thereof at an intensity and for a duration of time sufficient to produce a significant increase in a level of one or more stilbenes in the irradiated billets compared to a level of stilbenes in billets that are not irradiated;
    c) maintaining the irradiated sugarcane billets for at least about three days up to about 20 days; and
    d) selecting the irradiated sugarcane billets.

2. The method of claim 1, wherein the irradiated sugarcane billets are maintained in step (c) at a level of light that does not cause stilbene isomerization.

3. The method of claim 1, wherein the sugarcane billets range from about 2 mm to about 50 mm in thickness.

4. The method of claim 1, wherein the intensity of UVB light ranges from about 10 mW/cm2 to about 50 W/cm2.

5. The method of claim 1, wherein the intensity of UVC light ranges from about 1 mW/cm2 to about 25 mW/cm2.

6. The method of claim 1, wherein the duration of irradiation ranges from about 10 minutes to about 3 hours.

7. The method of claim 1, wherein the stilbene is resveratrol.

8. The method of claim 1, wherein the stilbene is piceatannol.

9. The method of claim 1, wherein the temperature during step (b) is maintained at a temperature between about 20 degrees Centigrade to about 40 degrees Centigrade.

10. The method of claim 1, wherein the temperature during step (c) is maintained at a temperature between about zero degrees Centigrade and to about 40 degrees Centigrade.

11. The method of claim 1, further comprising
e) extracting one or more stilbenes from the irradiated billets after step (c).

12. The method of claim 1, wherein the stilbenes are in the trans form.

13. The method of claim 1, wherein the sugarcane billets are maintained in step (c) from about 7 up to about 20 days after irradiation.

14. The method of claim 1, wherein the sugarcane billets in step (a) are obtained from sugarcane that was inoculated with a fungus that increases stilbene production in the sugarcane.

15. The method of claim 14, wherein the fungus is *Collectotrichum falcatum* or *Aspergillus sojae*.

16. The method of claim 1, wherein the sugarcane is a member selected from the group consisting of the variety cv L 97-128, cv HO95 and cv LCP.

17. Sugarcane billets made by the method according to claim 1.

18. The sugarcane billets of claim 17, wherein the stilbene is resveratrol ranging from about 10 µg/g to about 500 µg/g.

19. The sugarcane billets of claim 17, wherein the stilbene is piceatannol ranging from 100 µg/g to 10,000 µg/g.

20. The sugarcane billets of claim 17, wherein the sugarcane is a member selected from the group consisting of the variety cv L 97-128, cv HO95 and cv LCP.

21. Bagasse obtained from the sugarcane billets of claim 17.

22. Biofuel made from the bagasse of sugarcane billets of claim 17.

23. A method comprising
a) providing sugarcane leaves of a predetermined thickness;
b) irradiating the sugarcane leaves with Ultraviolet-C or Ultraviolet-B light or combinations thereof at an intensity and for a duration of time sufficient to produce a significant increase in a level of one or more stilbenes in the irradiated leaves compared to a level of stilbenes in leaves that are not irradiated; and
c) maintaining the irradiated sugarcane leaves for at least about three days before selecting the irradiated sugarcane leaves.

24. Sugarcane leaves made according to the method of claim 23.

25. A method, comprising
a) providing sugarcane billets between 2 mm and 50 mm in thickness;
b) maintaining the sugarcane for at least about three days up to about 20 days at a level of light that prevents stilbene isomerization at zero degrees Centigrade and to about 40 degrees Centigrade; and
c) then selecting the sugarcane billets, wherein the billets are enriched in stillbenes.

26. The sugarcane billets made by the method of claim 25.

* * * * *